(12) United States Patent
Wariar

(10) Patent No.: US 8,634,906 B2
(45) Date of Patent: *Jan. 21, 2014

(54) APPLICATION OF ELECTRIC FIELDS TO THE LUNG AS THERAPY FOR PULMONARY EDEMA

(71) Applicant: Cardiac Pacemakers, Inc., St. Paul, MN (US)

(72) Inventor: Ramesh Wariar, Blaine, MN (US)

(73) Assignee: Cardiac Pacemakers, Inc., St. Paul, MN (US)

(\*) Notice: Subject to any disclaimer, the term of this patent is extended or adjusted under 35 U.S.C. 154(b) by 0 days.

This patent is subject to a terminal disclaimer.

(21) Appl. No.: 13/731,812

(22) Filed: Dec. 31, 2012

(65) Prior Publication Data

US 2013/0123878 A1 May 16, 2013

Related U.S. Application Data

(63) Continuation of application No. 12/773,647, filed on May 4, 2010, now Pat. No. 8,359,093.

(60) Provisional application No. 61/176,199, filed on May 7, 2009.

(51) Int. Cl.
*A61B 5/053* (2006.01)

(52) U.S. Cl.
USPC ........................................... 600/547

(58) Field of Classification Search
USPC ................... 607/17, 36; 600/345, 529, 547
See application file for complete search history.

(56) References Cited

U.S. PATENT DOCUMENTS

| | | | |
|---|---|---|---|
| 5,284,136 A | 2/1994 | Hauck et al. | |
| 6,424,864 B1 | 7/2002 | Matsuura | |
| 6,512,949 B1 * | 1/2003 | Combs et al. | 600/547 |
| 7,387,610 B2 | 6/2008 | Stahmann et al. | |
| 8,359,093 B2 | 1/2013 | Wariar | |
| 2007/0282185 A1 | 12/2007 | Belalcazar | |
| 2008/0119907 A1 | 5/2008 | Stahmann | |
| 2008/0125826 A1 | 5/2008 | Belalcazar et al. | |
| 2008/0132971 A1 * | 6/2008 | Pille et al. | 607/50 |
| 2008/0183248 A1 | 7/2008 | Rezai et al. | |
| 2008/0294228 A1 | 11/2008 | Brooke et al. | |
| 2008/0306570 A1 | 12/2008 | Rezai et al. | |

(Continued)

FOREIGN PATENT DOCUMENTS

| | | |
|---|---|---|
| JP | 2007503278 A | 2/2007 |
| JP | 20080183248 A | 8/2008 |

(Continued)

OTHER PUBLICATIONS

"U.S. Appl. No. 12/773,647, Response filed Aug. 7, 2012 to Non Final Office Action mailed Apr. 24, 2012", 12 pgs.

(Continued)

*Primary Examiner* — Rex R Holmes
(74) *Attorney, Agent, or Firm* — Schwegman Lundberg & Woessner, P.A.

(57) ABSTRACT

System and method of applying electric fields to a patient's lung(s) to reduce pulmonary edema. The system includes a first electrode and a second electrode, at least one of which is associated with the lung. The electric field can be controlled so as to modulate a level of fluid in the lung.

20 Claims, 7 Drawing Sheets

(56) References Cited

U.S. PATENT DOCUMENTS

| | | | |
|---|---|---|---|
| 2009/0012416 A1 | 1/2009 | Belalcazar et al. | |
| 2009/0018599 A1 | 1/2009 | Hastings et al. | |
| 2009/0069708 A1* | 3/2009 | Hatlestad et al. | 600/547 |
| 2010/0286746 A1 | 11/2010 | Wariar | |

FOREIGN PATENT DOCUMENTS

| | | |
|---|---|---|
| JP | 20080306570 A | 12/2008 |
| JP | 2012515050 A | 7/2012 |
| WO | WO-2008066732 A1 | 6/2008 |
| WO | WO-2009005559 A1 | 1/2009 |
| WO | WO-2009035596 A1 | 3/2009 |
| WO | WO-2010129590 A1 | 11/2010 |

OTHER PUBLICATIONS

"U.S. Appl. No. 12/773,647, Examiner Interview Summary mailed Jul. 24, 2012", 3 pgs.

"U.S. Appl. No. 12/773,647, Non Final Office Action mailed Apr. 24, 2012", 8 pgs.

"U.S. Appl. No. 12/773,647, Notice of Allowance mailed Sep. 19, 2012", 7 pgs.

"Australian Application Serial No. 2010246028, Examination Report mailed Jul. 27, 2012", 3 pgs.

"International Application Serial No. PCT/US2010/033600, International Preliminary Report on Patentability mailed Nov. 17, 2011", 10 pgs.

"International Application Serial No. PCT/US2010/033600 Written Opinion mailed Jul. 23, 2010", 9 pgs.

"International Application Serial No. PCT/US2010/033600, International Search Report mailed Jul. 23, 2010", 6 pgs.

Blank, M., "Na,K-ATPase function in alternating electric fields.", FASEB J., 6(7), (Apr. 1992), 2434-8.

Chen, W., et al., "Entrainment of Na/K pumps by a synchronization modulation electric field.", J Bioenerg Biomembr., 39(4), (Aug. 2007), 331-9.

Hochberg, I., et al., "Patterns of alveolar fluid clearance in heart failure", Int J Cardiol., 130(2), Epub Jun. 24, 2008, (Nov. 12, 2008), 125-30.

Jackson, L. B., et al., "", Digital Filters and Signal Processing, (Second Edition), Kluwer Academic Publishers, Bostonl, MA, (1989), 332-340.

Liu, D. S, et al., "Activation of Na+ and K+ pumping modes of (Na,K)-ATPase by an oscillating electric field.", J Biol Chem., 265(13), (May 5, 1990), 7260-7.

Serpersu, E. H, et al., "Activation of electrogenic Rb+ transport of (Na,K)-ATPase by an electric field", J Biol Chem., 259(11), (Jun. 10, 1984), 7155-62.

Xie, T. D, et al., "Recognition and processing of randomly fluctuating electric signals by Na,K-ATPase", Biophys J. 67(3), (Sep. 199), 1247-51.

"Japanese Application Serial No. 2012-509913, Office Action mailed May 14, 2013", With English Translation, 4 pgs.

* cited by examiner

APPLICATION OF ELECTRIC FIELDS TO THE LUNG AS THERAPY FOR PULMONARY EDEMA

CLAIM OF PRIORITY

This application is a continuation of and claims the benefit of priority under 35 U.S.C. §120 to U.S. patent application Ser. No. 12/773,647, filed on May 4, 2010, now issued as U.S. Pat. No. 8,359,093, which claims the benefit of U.S. Provisional Application No. 61/176,199, filed on May 7, 2009, under 35 U.S.C. §119(e), each of which is hereby incorporated by reference in its entirety.

BACKGROUND

Pulmonary edema is a manifestation of fluid overload in patients suffering from congestive heart failure (CHF) and other heart, lung, and kidney disorders.

Overview

This document describes, among other things, a system and method of applying electric fields to a patient's lung(s) to reduce pulmonary edema. The system includes a first electrode and a second electrode, at least one of which is associated with the lung. The electric field can be controlled so as to modulate a level of fluid in the lung.

Example 1 describes a system. In this example, the system comprises an electric field generator circuit configured to be coupled to a first electrode and a second electrode, wherein at least one of the first electrode or the second electrode is configured to be associated with a lung of a subject, and wherein the electric field generator circuit is configured to generate an electric field, for application to the lung, that is capable of modulating a level of fluid in the lung; and a controller coupled to the electric field generator circuit and configured to control the electric field in the lung so as to modulate the level of fluid in the lung.

In Example 2, the system of Example 1 optionally comprises the at least one of the first and second electrode, and wherein the at least one of the first and second electrode is configured to be used to provide an electric field, for application to the lung, that is capable of modulating the level of fluid in the lung, and configured to be located at or near at least one of a lung, a heart, a thoracic vein, a thoracic artery, or a thoracic lymph node.

In Example 3, the system of one or more of Examples 1-2 optionally comprises the controller configured to control the electric field so as to controllably effect removal of fluid from the lung.

In Example 4, the system of one or more of Examples 1-3 optionally comprises controller configured to control the electric field so as to modulate a level of fluid in the lung by modulating alveolar Na,K-ATPase activity.

In Example 5, the system of one or more of Examples 1-4 optionally comprises the electric field generator circuit configured to generate an alternating electric field with field strength of about 5 microvolts/cm to about 50 millivolts/cm.

In Example 6, the system of one or more of Examples 1-5 optionally comprises the electric field generator circuit is configured to generate pulses at a frequency of about 1.0 MHz.

In Example 7, the system of one or more of Examples 1-6 optionally comprises a cardiac signal sensing circuit configured to sense an intrinsic cardiac signal, wherein the controller is coupled to the sensing circuit and configured to determine an absolute cardiac refractory period, and wherein the controller is configured to control the electric field generator circuit to deliver pulses substantially only during the absolute cardiac refractory period.

In Example 8, the system of one or more of Examples 1-7 optionally comprises a fluid monitoring circuit configured to monitor a level of fluid in the lung, wherein the controller is configured to control the electric field using information about the monitored level of fluid in the lung to control the level of fluid in the lung.

In Example 9, the system of one or more of Examples 1-8 optionally comprises the controller configured to control at least one of a magnitude, a pulsewidth, a frequency, a duration, a duty cycle, or a waveform morphology associated with the electric field to control the level of fluid in the lung.

In Example 10, the system of one or more of Examples 1-9 optionally comprises the controller configured to control the electric field in the lung using information from at least one implantable sensor including at least one of an implantable heart sound sensor, an implantable impedance sensor, an implantable physical activity sensor, an implantable respiration sensor, an implantable blood pressure sensor, an implantable electrocardiogram sensor, an implantable oxygen saturation sensor, an implantable blood flow sensor, or an implantable temperature sensor.

Example 11 describes a system. In this example, the system comprises an electric field generator circuit configured to be coupled to a first electrode and a second electrode, wherein at least one of the first electrode or the second electrode is configured to be associated with a lung of a subject, and wherein the electric field generator circuit is configured to generate an electric field, for application to the lung, that is capable of modulating a level of fluid in the lung; a controller coupled to the electric field generator circuit and configured to control the electric field in the lung so as to modulate the level of fluid in the lung; and a fluid monitoring circuit configured to monitor a level of fluid in the lung, and wherein the controller is configured to control the electric field using information about the monitored level of fluid in the lung to control the level of fluid in the lung.

In Example 12, the system of Example 11 optionally comprises the at least one of the first and second electrode, wherein the at least one of the first and second electrode is configured to provide an electric field located at or near at least one of a lung, a heart, a thoracic vein, a thoracic artery, or a thoracic lymph node; wherein the controller is configured to control the electric field so as to controllably effect removal of fluid from the lung by modulating alveolar Na,K-ATPase activity; wherein the electric field generator circuit is configured to generate an alternating electric field with field strength of about 5 microvolts/cm to about 50 millivolts/cm and a frequency of about 1.0 MHz; wherein the controller is coupled to a cardiac signal sensing circuit, configured to sense an intrinsic cardiac signal, and wherein the controller is configured to determine an absolute cardiac refractory period, and wherein the controller is configured to control the electric field generator circuit to deliver pulses substantially only during the absolute cardiac refractory period; wherein the controller is configured to control at least one of a magnitude, a pulsewidth, a frequency, a duration, a duty cycle, or a waveform morphology associated with the electric field to control the level of fluid in the lung; and wherein the controller is configured to control the electric field in the lung using information from at least one implantable sensor including at least one of an implantable heart sound sensor, an implantable impedance sensor, an implantable physical activity sensor, an implantable respiration sensor, an implantable blood pressure sensor, an implantable electrocardiogram sensor, an implantable oxygen saturation sensor, an implantable blood flow sensor, or an implantable temperature sensor.

Example 13 describes a method. In this example, the method comprises applying an electric field to a subject using a first electrode and a second electrode, at least one of the first electrode or the second electrode being associated with a lung of the subject; generating an electric field, for application to the lung, that is capable of modulating a level of fluid in the lung; and controlling the electric field to modulate the level of fluid in the lung.

In Example 14, the method of Example 13 optionally comprises using the first electrode and the second electrode in or near at least one of a lung, a heart, a thoracic vein, a thoracic artery, or a thoracic lymph node.

In Example 15, the method of one or more of Examples 13-14 optionally comprises modulating alveolar Na,K-ATPase activity so as to controllably effect removal of fluid from the lung.

In Example 16, the method of one or more of Examples 13-15 optionally comprises providing an alternating electric field with field strength of about 5 microvolts/cm to about 50 millivolts/cm.

In Example 17, the method of one or more of Examples 13-16 optionally comprises providing pulses at a frequency of about 1.0 MHz.

In Example 18, the method of one or more of Examples 13-17 optionally comprises sensing an intrinsic cardiac signal; determining an absolute cardiac refractory period; and delivering electric pulses substantially only during the absolute cardiac refractory period.

In Example 19, the method of one or more of Examples 13-18 optionally comprises monitoring a level of fluid in the lung; and wherein the controlling the electric field includes controlling the electric field using information about the monitored level of fluid in the lung to control the level of fluid in the lung.

In Example 20, the method of one or more of Examples 13-19 optionally comprises controlling at least one of a magnitude, a pulsewidth, a frequency, a duration, a duty cycle, or a waveform associated with the electric field to control the level of fluid in the lung.

In Example 21, the method of one or more of Examples 13-20 optionally comprises using information from at least one implantable sensor including an implantable heart sound sensor, an implantable impedance sensor, an implantable activity sensor, an implantable respiration sensor, an implantable blood pressure sensor, an implantable electrocardiogram sensor; an implantable oxygen saturation sensor, an implantable blood flow sensor, or an implantable temperature sensor.

This overview is intended to provide an overview of subject matter of the present patent application. It is not intended to provide an exclusive or exhaustive explanation of the invention. The detailed description is included to provide further information about the present patent application.

DETAILED DESCRIPTION

This document describes, among other things, applying electric fields to a patient's lung(s) to reduce pulmonary edema through modulation of a fluid level in the lung.

Figure 1:
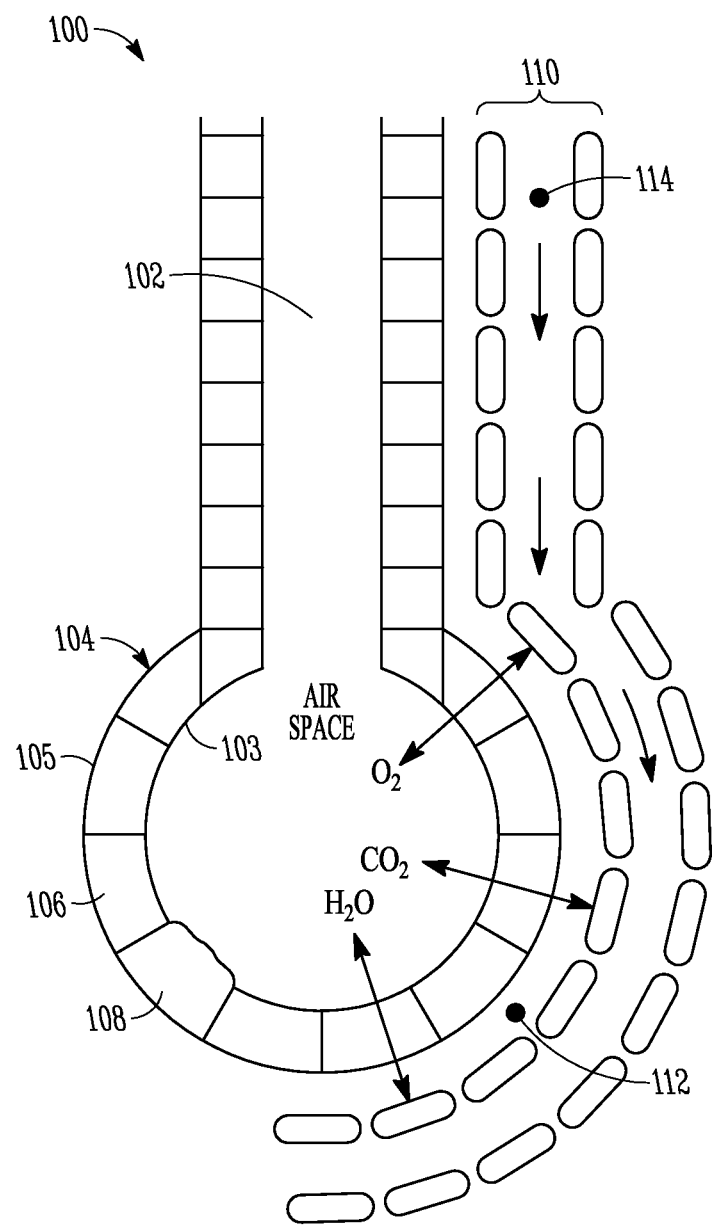
FIG. 1 is a diagram illustrating generally an example of an alveolus.

FIG. 1 is a diagram illustrating generally an example of an alveolus 100. Alveoli are tiny air sacs inside the lung where the exchange of oxygen and carbon dioxide takes place between blood and air. Alveoli are found in clusters at the furthest end of each bronchiole 102 in the lung. The walls of alveoli, called alveolar epithelium 104, are one-cell thick. Surrounding each alveolus is a network of capillaries 110 carrying venous blood 114. Inhaled oxygen in the alveolar air space diffuses across the alveolar epithelium 104, through the interstitium 112, and into the blood 114 circulating through the capillaries 110. Likewise, carbon dioxide in the blood 114 diffuses into the alveoli and is eventually exhaled.

The alveolar epithelium 104 is composed of two main cell types, type I 106 and type II 108. Alveolar type I epithelial cells 106, which account for about 95% of all alveolar epithelial cells, facilitate gas exchange by minimizing the diffusion distance from alveolar gas to the blood. Type II cells 108, which account for the remaining 5% of alveolar epithelial cells, have the ability to secrete surfactant, maintain the alveolar epithelium, and recover from injury by proliferating and differentiating into type I cells 106.

Figure 2:
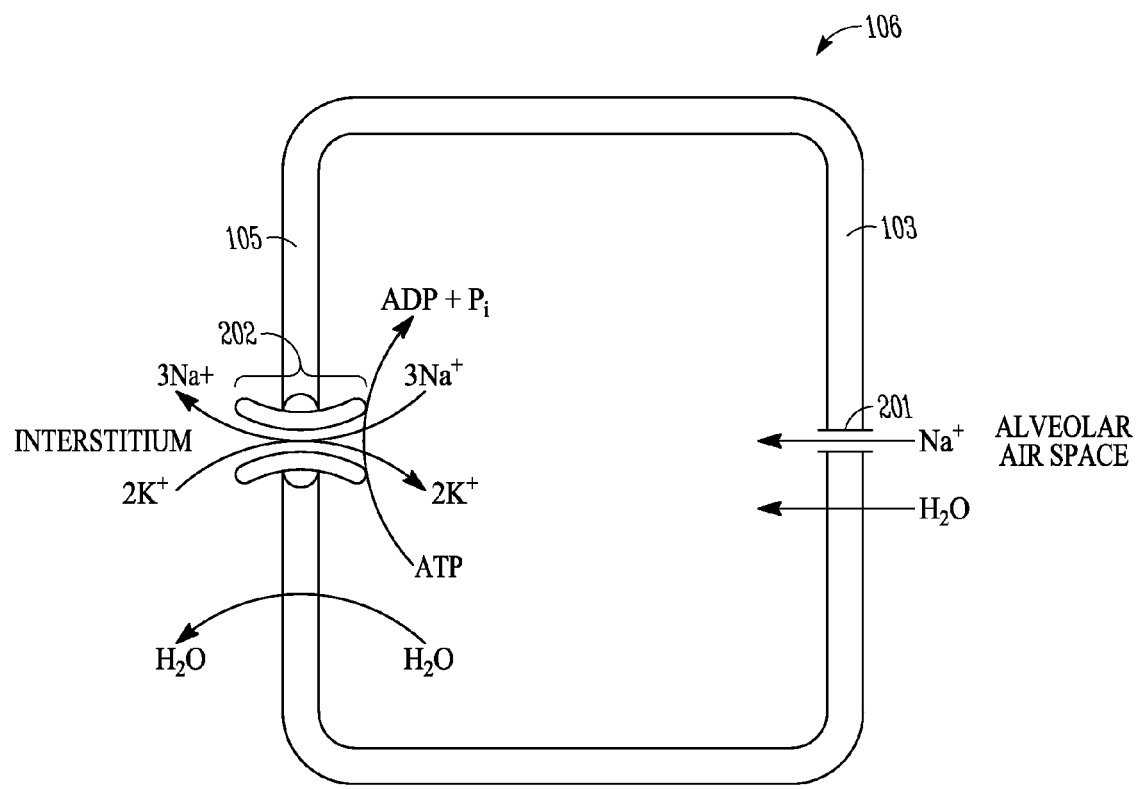
FIG. 2 is a diagram illustrating generally a more detailed example of a type I alveolar cell.

FIG. 2 is a diagram illustrating generally a more detailed example of a type I alveolar cell 106. The type I cell 106 contains an apical membrane domain 103 and basolateral membrane domain 105. The apical domains 103 have short microvilli (not shown) and comprise different pathways for ion transport, predominantly, the apical sodium ion channels 201, whereas the basolateral domains 105 are abundant with Na$^+$,K$^+$-ATPase pumps 202. Na$^+$,K$^+$-ATPase 202, the membrane enzyme responsible for establishing ion gradients across cell membranes, catalyzes the coupled transport of three sodium ions from inside out and two potassium ions from outside in for each ATP split.

Referring now to FIGS. 1 and 2, fluid overload (such as in CHF patients) can result in changes in the hydrostatic and oncotic pressure gradients across the pulmonary capillary 110 circulation, leading to pulmonary edema. Pulmonary edema is characterized by fluid in the alveolar air space, which impairs gas exchange and can become life threatening. In response to pulmonary edema, the cells of the alveolar epithelium 104 clear the fluid via resorption. Active sodium transport through the basolateral Na$^+$,K$^+$-ATPase 202 of alveolar cells, followed by the movement of water out of the alveolar space caused by the osmotic gradient, serves as a major defense mechanism that keeps the alveolar air spaces free of edema. In this way, water inside the alveolar air space moves out into the interstitium 112, and eventually into the blood 114 circulating in the pulmonary capillaries 110, thus reducing pulmonary edema. In patients with chronic CHF, Na$^+$,K$^+$-ATPase 202 activity in the alveolar epithelium 104 may be upregulated in order to keep the alveolar spaces free of edema (see, e.g., Hochberg et al., Patterns of alveolar fluid clearance in heart failure, International Journal of Cardiology 2008).

Figure 3:
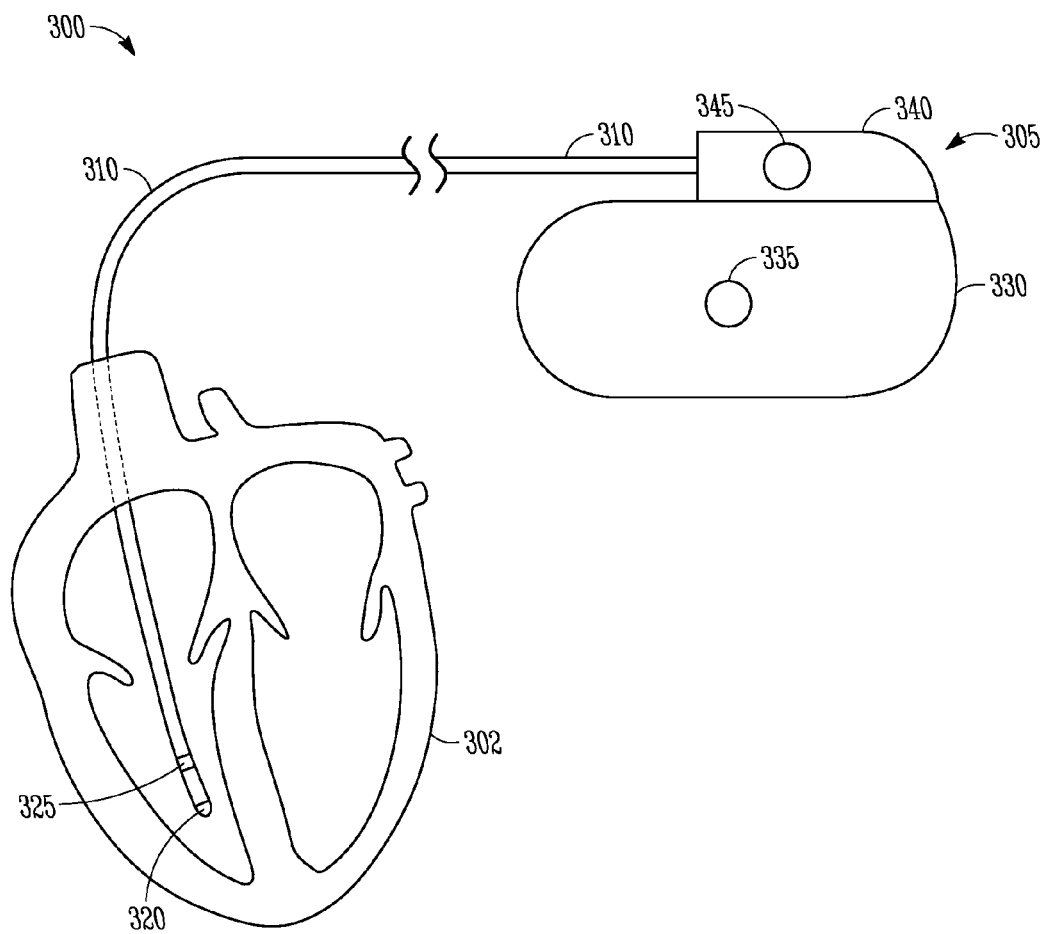
FIG. 3 is an illustration of an example of an implantable medical device including a cardiac function management device with leadwires going to the heart.

FIG. 3 illustrates an example of a cardiac function management system 300. In this example, the system 300 can include, among other things, a cardiac function management device ("CFM") 305 and a leadwire ("lead") 310 for communicating signals between the device 305 and a portion of a living organism, such as a heart 302. Examples of the device 305 can include bradycardia and antitachycardia pacemakers, cardioverters, defibrillators, combination pacemaker/defibrillators, neuromodulation devices, drug delivery devices, or any other cardiac rhythm management apparatus capable of monitoring cardiovascular function or providing cardiovascular therapy such as for benefit of the heart 302. The system 300 can also include additional components such as, for example, a local or remote programmer capable of communicating with the device 305.

In an example, the system 300 can be implantable in a living organism, such as in a pectoral region of a human patient, or elsewhere. In an example, one or more portions of the system 300 (e.g., device 305) can be disposed external to the human patient. In the illustrated example, portions of the lead 310 are disposed in the right ventricle; however, any other positioning of lead 310 can be used. For example, lead 310 can be positioned in a location that is associated with the right atrium, the superior vena cava, the coronary sinus or great cardiac vein, the left atrium or ventricle, epicardially, or elsewhere. In an example, the lead 310 can include commercially available unipolar or bipolar pacing leads. The system 300 can also include one or more other leads or electrodes (e.g., with a lead, or leadless), such as in addition or alternative to lead 310, appropriately disposed, such as in or around the heart 302, or elsewhere. An example of leadless electrostimulation electrodes is described in Hastings et al. U.S. Patent Publication No. 2009/0018599 entitled "CARDIAC STIMULATION USING LEADLESS ELECTRODE ASSEMBLIES," the disclosure of which is incorporated herein by reference in its entirety.

In an example, the system 300 can include at least four electrodes such as for sensing a thoracic impedance indicative of fluid status. An example of impedance sensing using four electrodes is described in Hauck et al. U.S. Pat. No. 5,284,136 entitled "DUAL INDIFFERENT ELECTRODE PACEMAKER," assigned to the assignee of the present patent application, the disclosure of which is incorporated herein by reference in its entirety, including its description of an impedance sensing system. The present systems and methods can also include using a different number of electrodes (e.g., 2 or 3 electrodes, or more than 4 electrodes). In an example, a first conductor of the multiconductor lead 310 can electrically couple a first electrode, such as a tip electrode 320 (e.g., disposed at the apex of the right ventricle of the heart 302), to the device 305. A second conductor of the multiconductor lead 310 can independently electrically couple a second electrode, such as a ring electrode 325, to the device 305.

In an example, the device 305 can include a hermetically sealed housing 330, formed from a conductive metal, such as titanium. The housing 330 (also referred to as a "case" or "can") can be substantially covered over its entire surface by a suitable insulator, such as silicone rubber, except for at a window that forms a third electrode, referred to as a "case" or a "can" electrode 335. In an example, a header 340 can be mounted on the housing 330 such as for receiving the lead 310. The header 340 can be formed of an insulative material, such as molded plastic. The header 340 can also include at least one receptacle, such as for receiving the lead 310 and electrically coupling conductors of the lead 310 to the device 305. The header 340 can also include a fourth electrode, which can be referred to as an indifferent electrode 345.

Figure 4:
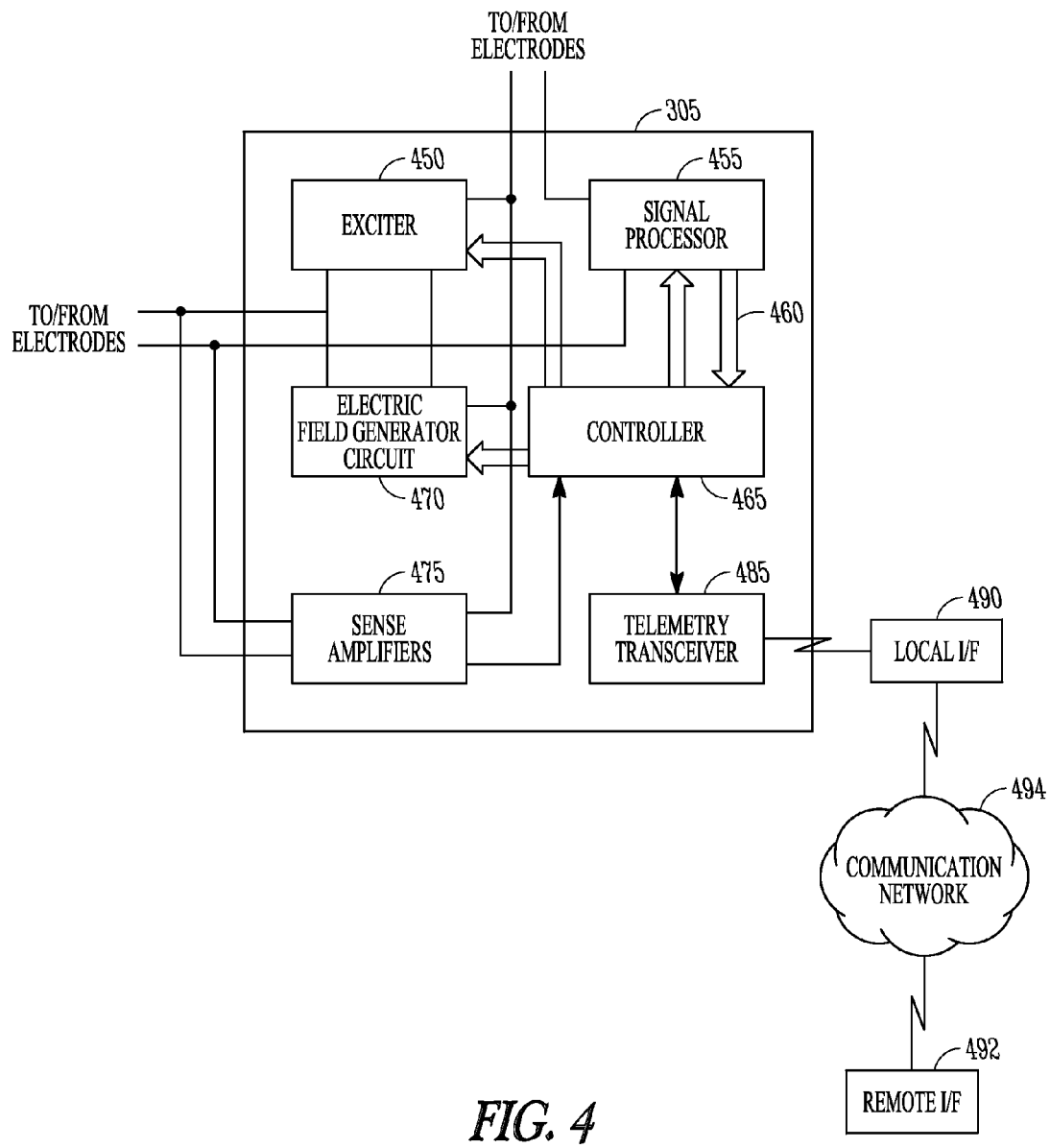
FIG. 4 is a block diagram illustrating an example of portions of the implantable medical device together with schematic illustrations of connections to the various electrodes.

FIG. 4 illustrates generally portions of the device 305, together with schematic illustrations of connections to the various electrodes. The device 305 can include an electrical stimulation source, such as an exciter 450. The exciter 450 can deliver an electrical excitation signal, such as a strobed sequence of current pulses or other measurement stimuli, to the heart 302 (e.g., between the ring electrode 325 and the tip electrode 320, or using any other electrode configuration suitable for delivering the current pulses). The exciter 450 can be configured to receive one or more clock or other control signals from a controller 465. In response to the excitation signal provided by the exciter 450, a response signal can be sensed by signal processor 455 (e.g., between the tip electrode 320 and the indifferent electrode 345, or any other suitable electrode configuration). In an example, the response signal sensed by the signal processor 355 can be a voltage that represents a transthoracic (e.g., across a portion of the chest or thorax) impedance.

An example of an approach for measuring transthoracic impedance is described in Stahmann et al. U.S. Pat. No. 7,387,610 entitled "THORACIC IMPEDANCE DETECTION WITH BLOOD RESISTIVITY COMPENSATION," assigned to the assignee of the present application, the disclosure of which is incorporated herein by reference in its entirety, including its description of an approach for measuring impedance, such as for the present application of measuring transthoracic impedance.

In an example, an impedance-derived fluid status signal can be obtained by measuring transthoracic (across the chest or thorax) impedance. For example, a transthoracic impedance can be measured to obtain a fluid status indicator of a pulmonary fluid status associated with pulmonary edema. The fluid status indicator can be monitored by a fluid status monitoring circuit which includes the exciter 450, the signal processor 455, and electrodes 320 and 325, for example.

The controller 465 can be configured to use information about the fluid status indicator to control therapy provided by the electric field generator circuit 470. In an example, the controller 465 can be configured to control the electric field provided by the electric field generator circuit 470 so as to modulate a level of fluid in the lung by modulating alveolar Na, K-ATPase activity. For example, application of an alternating electric field with field strength of 5 microvolts/cm to 50 millivolts/cm and frequency of 1.0 MHz can activate the Na$^+$ pumping mode of Na, K-ATPase in human erythrocytes. By applying a similar electric field to alveolar cells, it is believed that an activated Na$^+$ pumping mode of Na, K-ATPase can increase the transport of sodium and water out of the alveolar air space (as described above with respect to FIGS. 1 and 2), thereby reducing the level of pulmonary edema. In addition to using information about the fluid status in the lung, the controller circuit 465 can also use information from other implanted sensors to control the electric field provided by the electric field generator circuit 470. Examples of these additional sensors include a heart sound sensor, impedance sensor, physical activity sensor, respiration sensor, blood pressure sensor, electrocardiogram sensor, oxygen saturation sensor, blood flow sensor, and temperature sensor.

In the example shown in FIG. 4, the electric field generator circuit 470 is included within the cardiac function management device 305. In another example, the electric field generator circuit 470 can be part of a separate implanted or external device. If the electric field generator circuit 470 is part of a separate device, the device 305 can communicate with that separate device. This can include direct communication between two devices in or on the human body, wherein such communication can be carried out within the human body, such as via inductive coupling, ultrasonic communication, or using body tissue as an electrical conductor, as illustrative examples. It can additionally or alternatively include indirect communication between two implanted devices, or between an implanted and an external device, such as by using a local or remote external device as an intermediary for performing the communication. An illustrative example can include communicating between an implanted device 305 and a therapy circuit located in a separately implanted device, such as by using the Boston Scientific Corp. (Cardiac Pacemakers, Inc.) LATITUDE® System, which can automatically collect information from a subject's implanted medical device 305 and communicate the information to a another one of the subject's implanted or ambulatory personal medical device, such as via a local external interface 490 that can be communicatively coupled via a communication network 494 to a secure remote computer 492.

FIG. 4 also illustrates an example of sense amplifiers 475, one or more of which can be used to monitor electrical heart activity within the subject, such as for synchronizing the delivery of electric pulses from the electric field generator circuit 470 with an absolute refractory period of the cardiac cycle, as discussed below. In addition, FIG. 4 illustrates a telemetry transceiver 485, which can be configured to receive information from the controller 465 (e.g. information about the first and second fluid status indicators, or information about controlling the therapy) and communicate the information, such as through a unidirectional or bidirectional wireless communication link with an external local interface 490. In certain examples, the external local interface 490 can further unidirectionally bidirectionally communicate with an external remote interface 492, wirelessly or otherwise, such as via a shared communication or computer network 494. The remote interface 492 can be configured to provide an alert or alarm, such as to predict heart failure decompensation, thereby allowing for home monitoring or remote monitoring of a subject by a physician or other health care provider.

Figure 5:
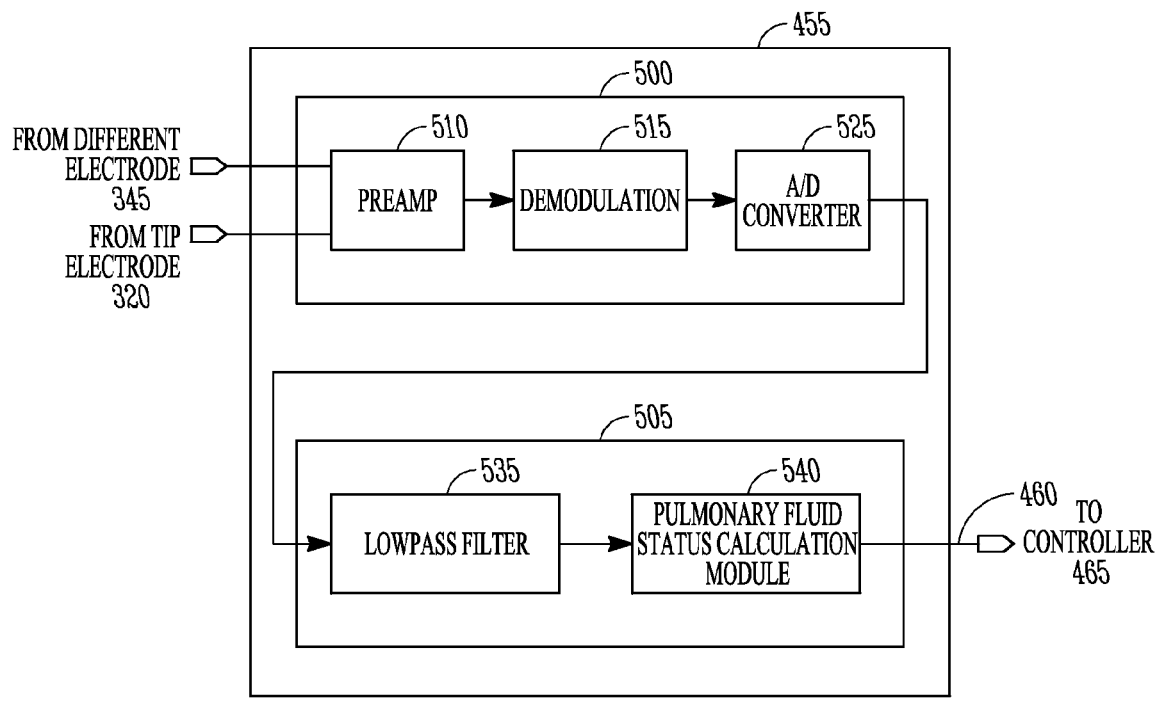
FIG. 5 is a block diagram illustrating generally an example of portions of a signal processor.

FIG. 5 illustrates generally an example of one or more portions of the signal processor 455. The signal processor 455 can include an analog signal processing circuit 500 and a digital signal processing circuit 505. Inputs of a preamplifier 510 (also referred to as a preamp or a receiver) of an analog signal processing circuit 500 can be electrically coupled to the indifferent electrode 345 and the tip electrode 320 such as for receiving a signal in response to the above-described stimuli provided by the exciter 450. The analog signal processing circuit 500 can also include a demodulator 515, such as receiving the output of the preamplifier 510, and providing an output signal to a lowpass filter 535. The output signal from the lowpass filter 535 can be received by an analog-to-digital (A/D) converter 525.

In an example, the A/D converter 525 can be implemented as a 12-bit, successive approximation type switched-capacitor A/D converter having an input range of approximately 1 Volt. In one example, A/D converter 525 provides one 12-bit word corresponding to a sequence of current pulses delivered by exciter 450. Many different implementations of A/D converter 525 can be suitable for use in the present systems and methods.

In an example, the lowpass filter 535 can include a single-pole infinite impulse response (IIR) digital filter that can receive a 12-bit digital output signal from the A/D converter 525. The lowpass filter 535 can attenuate or remove frequency components above its lowpass cutoff frequency of approximately 0.1 Hz, such as to obtain thoracic fluid status information at lower frequencies. Many other different examples of the lowpass filter 535 can also be suitable for use in the present systems and methods. The lowpass filter 535 can advantageously attenuate frequency components of the signal that exceed the lowpass cutoff frequency of the lowpass filter 535. Attenuated frequencies can include the cardiac stroke signal, resulting from changes in blood volume in heart 302 as it contracts during each cardiac cycle, which appears as a component of the transthoracic impedance signal. In an example, the lowpass cutoff frequency of the filter 535 can be adaptively based on a heart rate or breathing rate of the patient. In an example, the lowpass cutoff frequency can be independent of any heart rate or breathing rate signal obtained from the patient. In an example, the lowpass filter 535 can use a Chebyshev filter. In an example, the lowpass filter 535 can include an Elliptic filter. In an example, the lowpass filter 535 can use a state-space structure, rather than a conventional direct form structure. The state-space structure can further reduce the effects of coefficient quantization and round-off noise. An example of such a state-space structure is described in Leland B. Jackson, "Digital Filters and Signal Processing," $2^{nd}$ ed., pp. 332-340, Kluwer Academic Publishers, Boston, Mass., the disclosure of which is incorporated herein by reference.

In an example, a digital signal processing circuit 505 can be included within the controller 465 such as, for example, as a sequence of instructions executed by a microprocessor. In an example, the digital signal processing circuit 505 can include separately implemented hardware portions dedicated to performing the digital signal processing tasks described herein. A pulmonary fluid status calculation module 540 can receive an output signal from the lowpass filter 535, and can provide a resulting fluid status indicator at node 460 to the controller 465, such as explained below. In an example, a pulmonary fluid status calculation module 540 can be implemented as a sequence of instructions executed on any suitable microprocessor. In an example, the pulmonary fluid status calculation module 540 can be implemented as any other hardware or software configuration capable of calculating a fluid status indicator based on impedance-derived fluid status information.

In an example, the pulmonary fluid status calculation module 540 can include a comparator, such as for comparing the lowpass-filtered pulmonary impedance signals to a threshold value. An output of the comparison can be used to provide a pulmonary fluid status indicator, for example, indicating excess fluid in the lungs when its impedance falls below a specified threshold value. In an example, the specified threshold value can be specified using a long-term or other baseline value of the impedance, such as obtained from the subject during a normal condition (e.g., no edema). For example, the specified threshold value can be specified as an offset from such normal condition value. In an example, the specified threshold value can be specified using a value obtained during abnormal conditions, such as during a decompensation episode, or a time period preceding an associated decompensation episode.

In an example, a difference or ratio between a long-term average (or other baseline measure of central tendency) and a short-term average (or other more acute measure of central tendency) can be used as a pulmonary fluid status indication, or compared to a threshold value or otherwise signal-processed to obtain a resulting pulmonary fluid status indication.

In an example, a histogram approach can be used to determine pulmonary fluid status. An example of such a histogram approach is described in Hatlestad et al. U.S. Patent Publication Ser. No. 11/853,590, entitled "HISTOGRAM-BASED THORACIC IMPEDANCE MONITORING," filed on Sep. 11, 2007, which is incorporated by reference herein in its entirety, including its discussion of using a histogram approach to determine fluid status.

Figure 6:
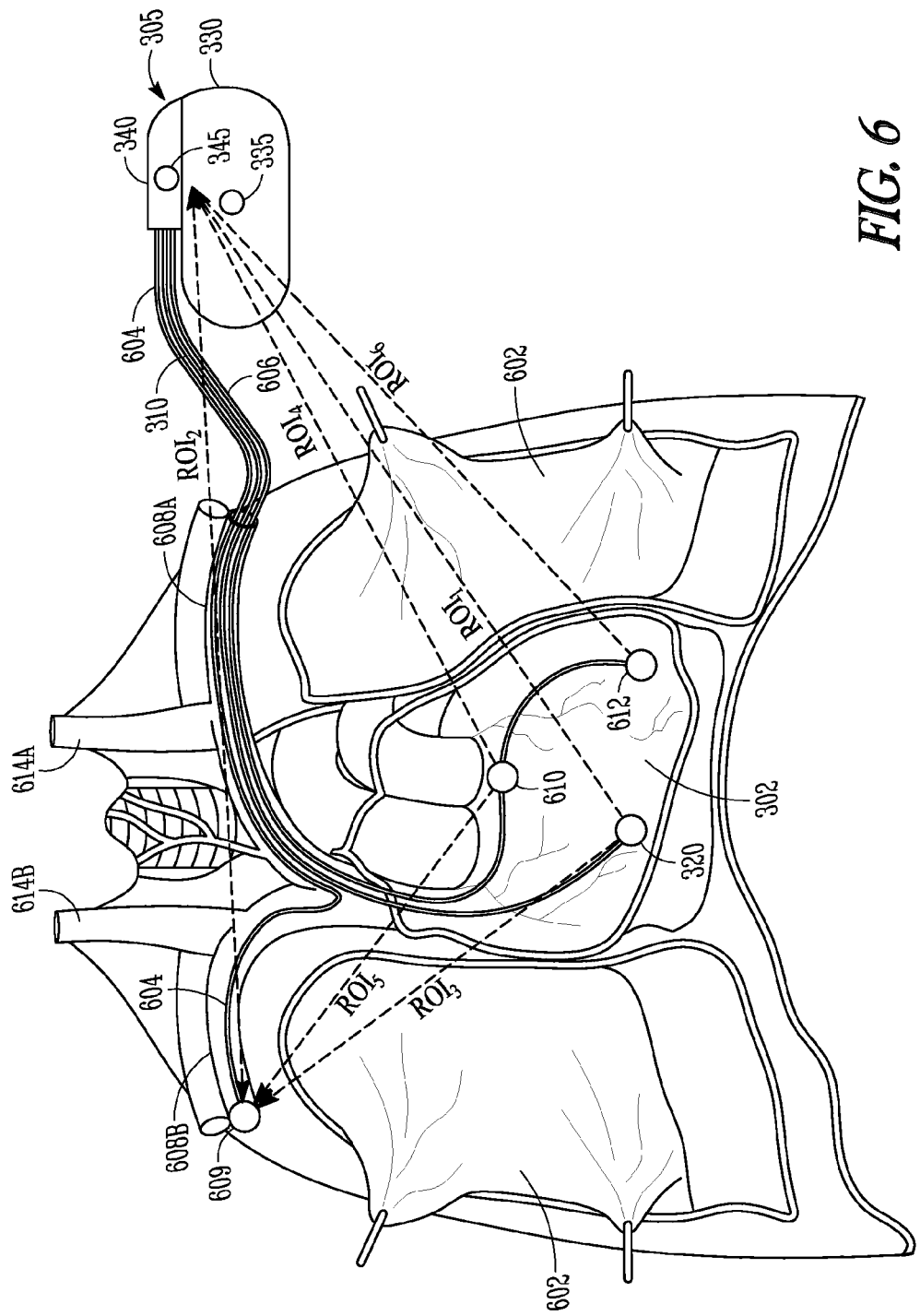
FIG. 6 is a diagram illustrating generally examples of different electrode configurations for measuring impedance-derived pulmonary fluid status signals and for providing electric field therapy to a thoracic region of interest.

FIG. 6 is a diagram illustrating generally examples of different electrode configurations such as for measuring impedance-derived pulmonary fluid status signals or for providing electric field therapy to a thoracic region of interest. The example of FIG. 6 can include the CFM device 305 such as described above with respect to FIG. 3, including the can 330, the can electrode 335, the header 340, and the indifferent electrode 345. FIG. 6 also includes the lead 310, the tip electrode 320 of which can be disposed at the apex of the right ventricle of the heart 302, such as described above with respect to FIG. 3. In addition, FIG. 6 illustrates other portions of the thoracic cavity, including the lungs 602, the left subclavian vein 608A, the right subclavian vein 608B, the left jugular vein 614A, and the right jugular vein 614B. The device 305 can be configured to receive the lead 604 and the lead 608, for example, in addition to the lead 310. In an example, the lead 604 can intravascularly electrically couple the electrode 609, located in the right subclavian vein 614B, to the device 305. In an example, the lead 606 can intravascularly electrically couple the electrode 610, located in the right atrium of the heart 302, and the electrode 612, located in association with the left ventricle of the heart 302 (e.g., in a coronary sinus or great cardiac vein), to the device 305.

Different combinations of the above-described examples of electrodes in FIG. 6 can be used to obtain thoracic impedance-derived measurements of pulmonary edema or other thoracic fluid status. Also, as shown in FIG. 6 by the dashed lines, different sets of electrodes can be used to generate different electric fields along different vectors, or regions of interest. Thoracic impedance-sensing can be conducted such as described above with respect to FIG. 3, such as between two or more electrodes located at or near opposite sides of one or both of the lungs 602.

For treating pulmonary fluid accumulation, a therapeutic electric field can be generated between two or more electrodes. This can involve using the electric field generator circuit 470, such as to generate a therapeutic alternating electric field with field strength of about 5 microvolts/cm to about 50 millivolts/cm and frequency of about 1.0 MHz, such as described above with respect to FIG. 4. The therapeutic alternating electric field can be provided, such as to one or more of the following regions of interest by using an appropriate electrode configuration, such as: (1) a first possible region of interest, $ROI_1$, such as by providing the therapeutic electric field between (a) the electrodes 335 and/or 345 and (b) the electrode 320; (2) a second possible region of interest, $ROI_2$, such as by providing the therapeutic electric field between (a) the electrodes 335 and/or 345 and (b) the electrode 609; (3) a third possible region of interest, $ROI_3$, such as by providing the therapeutic electric field between (a) the electrode 609 and (b) the electrode 320; (4) a fourth possible region of interest, $ROI_4$, such as by providing the therapeutic electric field between (a) the electrodes 335 and/or 345 and (b) the electrode 610; (5) a fifth possible region of interest, $ROI_5$, between (a) electrode 609 and (b) electrode 610; or (6) a sixth possible region of interest, $ROI_6$, between (a) the electrodes 335 and/or 345 and (b) the electrode 612. Such vectors can also be used for performing impedance sensing across the corresponding regions of interest, such as to determine pulmonary fluid status, based upon which the therapeutic alternating electric field is applied, withheld, or adjusted. Furthermore, electrode configurations other than those shown in FIG. 6 can also be used to sense impedance or provide therapeutic electric field pulses such as in one or more other regions of interest within the thoracic cavity. Such electrodes can be located in the right or left cephalic vein, subcutaneously placed in the right or left pectoral region, located in the left atrium, or located in the pulmonary arteries or pulmonary veins, for example.

Figure 7:
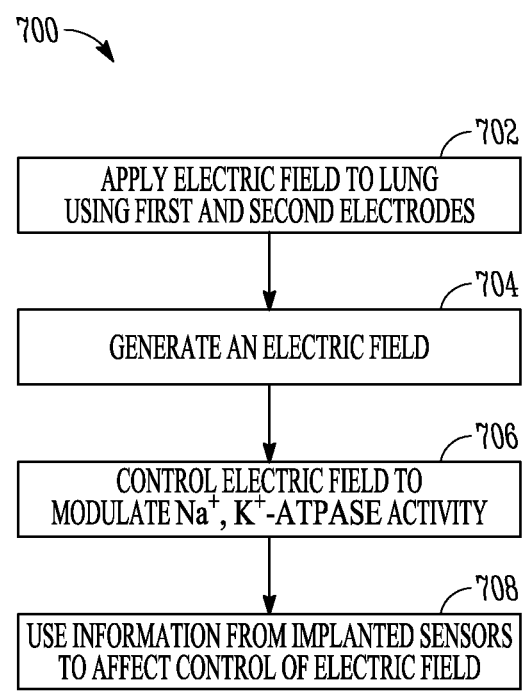
FIG. 7 is a chart illustrating generally an example of a method for applying an electric field to a lung to modulate a level of fluid in the lung.

FIG. 7 is a flow chart illustrating generally an example of a method 700 for applying an electric field to a lung to modulate a level of fluid in the lung. At 702, an electric field is applied to the lung using a first electrode and a second electrode. The electrodes can be associated with an implantable cardiac rhythm management device. At least one of the first or second electrodes can be implantably associated with the lung, and the electrodes can be located in or near at least one of an implantable cardiac rhythm management device, a heart, a lung, a thoracic vein, a thoracic artery, or a thoracic lymph node. More than two electrodes can be can be used to generate different electric fields along different vectors. The electric field can include alternating current with a field strength of about 5 microvolts/cm to about 50 millivolts/cm and a frequency of about 1.0 MHz. In some examples, the waveform morphology associated with the electric field can include a sine wave, a square wave, or a pseudorandom binary wave. Additionally, the electric field can be applied only during only during an absolute cardiac refractory period, or during one or more of an absolute cardiac refractory period and a period that is not an absolute cardiac refractory period. At 704, an electric field is generated and applied to the lung using the first and second electrodes. At 706, the electric field is controlled such that Na,K-ATPase activity in alveolar cells is modulated. The electric field can be controlled by modulating at least one of a magnitude, pulsewidth, frequency, duration, or waveform associated with the electric field. Furthermore, it is believed that controlling the electric field to modulate Na,K-ATPase activity in alveolar cells can result in the removal of fluid from the lung. As shown at 708, control of the electric field, and thus modulation of Na,K-ATPase activity in alveolar cells, can be affected by information provided by various implanted sensors, such as a lung fluid sensor, heart sound sensor, impedance sensor, physical activity sensor, respiration sensor, blood pressure sensor, electrocardiogram sensor, oxygen saturation sensor, blood flow sensor, and temperature sensor. For example, the delivery of electric pulses can be synchronized to the occurrence of a physiological event or condition sensed by one or more the implanted sensors. Examples of sensed physiological events or conditions to which the delivery of electric pulses can be synchronized include: pulmonary edema sensed by a lung fluid sensor or a thoracic impedance sensor; respiration cycle events, such as end inspiration or end expiration, sensed by a respiration sensor; patient posture, including the supine position, sensed by a posture sensor; increased cardiac filling pressure sensed by a pulmonary artery pressure sensor; and the presence or intensity of an $S_3$ heart sound sensed by a heart sound sensor. In addition to using information from implanted sensors to synchronize the delivery of electric pulses, electric pulse delivery can also be synchronized to external events, such as patient diuretic intake or physician input via the LATITUDE® System, for example.

Additional Notes

In this document, certain examples have been described with respect to "sodium" and "potassium" levels for illustrative clarity. The terms "sodium" and "potassium," as used in this document, can be used to refer to "sodium ions" and "potassium ions," respectively, without departing from the scope of the described systems or methods. Similarly, the terms "sodium" and "salt," as used in this document, can be used interchangeably to refer to "sodium ions" without departing from the scope of the described systems or methods.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device comprising:
   an electric field generator circuit configured to generate an electric field for application to a lung of a subject, the electric field being capable of modulating a level of fluid in the lung; and
   a controller coupled to the electric field generator circuit and configured to control the electric field in the lung so as to use the electric field to modulate the level of fluid in the lung, wherein the controller is configured to apply the electric field to alveolar cells of the lung at an electric field level that is of sufficient magnitude to controllably effect removal by the alveolar cells of the fluid from the lung.

2. The device of claim 1, wherein the controller is configured to control the electric field so as to modulate a level of fluid in the lung by modulating alveolar Na,K-ATPase activity.

3. The device of claim 1, comprising a cardiac signal sensing circuit configured to sense an intrinsic cardiac signal, wherein the controller is:
   coupled to the sensing circuit and configured to determine an absolute cardiac refractory period; and
   configured to control the electric field generator circuit to deliver pulses substantially only during the absolute cardiac refractory period.

4. The device of claim 1, comprising a fluid monitoring circuit configured to monitor a level of fluid in the lung, wherein the controller is configured to control the electric field using information about the monitored level of fluid in the lung to control the level of fluid in the lung.

5. The device of claim 1, wherein the electric field generator circuit is configured to generate an alternating electric field with field strength of about 5 microvolts/cm to about 50 millivolts/cm.

6. The device of claim 1, wherein the electric field generator circuit is configured to generate pulses at a frequency of about 1.0 MHz.

7. The device of claim 1, wherein the controller is configured to control at least one of a magnitude, a pulsewidth, a frequency, a duration, a duty cycle, or a waveform morphology associated with the electric field to control the level of fluid in the lung.

8. The device of claim 1, wherein the controller is configured to control the electric field in the lung using information from at least one implantable sensor including at least one of an implantable heart sound sensor, an implantable impedance sensor, an implantable physical activity sensor, an implantable respiration sensor, an implantable blood pressure sensor, an implantable electrocardiogram sensor, an implantable oxygen saturation sensor, an implantable blood flow sensor, or an implantable temperature sensor.

9. The device of claim 1, wherein the electric field generator circuit is configured to be coupled to a first electrode and a second electrode, wherein at least one of the first electrode or the second electrode is configured to be associated with the lung of the subject.

10. A method comprising:
   generating and applying an electric field to a lung of a subject, the electric field being capable of modulating a level of fluid in the lung; and
   controlling the electric field to modulate the level of fluid in the lung, wherein controlling the electric field includes applying the electric field to alveolar cells of the lung at an electric field level that is of sufficient magnitude to modulate alveolar Na,K-ATPase activity to controllably effect removal by alveolar cells of the fluid from the lung.

11. The method of claim 10, comprising:
   sensing an intrinsic cardiac signal;
   determining an absolute cardiac refractory period; and
   delivering electric pulses substantially only during the absolute cardiac refractory period.

12. The method of claim 10, comprising monitoring a level of fluid in the lung, wherein the controlling the electric field includes controlling the electric field using information about the monitored level of fluid in the lung to control the level of fluid in the lung.

13. The method of claim 10, wherein applying an electric field includes providing an alternating electric field with field strength of about 5 microvolts/cm to about 50 millivolts/cm.

14. The method of claim 10, wherein the applying an electric field includes providing pulses at a frequency of about 1.0 MHz.

15. The method of claim 10, wherein the controlling the electric field includes controlling at least one of a magnitude, a pulsewidth, a frequency, a duration, a duty cycle, or a waveform associated with the electric field to control the level of fluid in the lung.

16. The method of claim 10, wherein applying the electric field to the subject includes applying the electric field using a first electrode and a second electrode, at least one of the first electrode or the second electrode being associated with a lung of the subject.

17. The method of claim 16, wherein applying the electric field includes using the first electrode and the second electrode in or near at least one of a lung, a heart, a thoracic vein, a thoracic artery, or a thoracic lymph node.

18. A device-readable medium including instructions that, when performed by a device, cause the device to perform acts comprising:
   generating and applying an electric field to a lung of a subject, the electric field being capable of modulating a level of fluid in the lung; and
   controlling the electric field to modulate the level of fluid in the lung, wherein controlling the electric field includes applying the electric field to alveolar cells of the lung at an electric field level that is of sufficient magnitude to modulate Na,K-ATPase activity to controllably effect removal by alveolar cells of the fluid from the lung.

19. The device-readable medium of claim 18, including instructions that, when performed by the device, cause the device to perform acts comprising:
   sensing an intrinsic cardiac signal;
   determining an absolute cardiac refractory period; and
   delivering electric pulses substantially only during the absolute cardiac refractory period.

20. The device-readable medium of claim 18, including instructions that, when performed by the device, cause the device to perform acts comprising monitoring a level of fluid in the lung, wherein the controlling the electric field includes controlling the electric field using information about the monitored level of fluid in the lung to control the level of fluid in the lung.

* * * * *